US012558055B2

(12) United States Patent
Chou et al.

(10) Patent No.: US 12,558,055 B2
(45) Date of Patent: Feb. 24, 2026

(54) SMART NOISE REDUCTION DEVICE AND THE METHOD THEREOF

(71) Applicant: Decentralized Biotechnology Intelligence Co., Ltd., Taipei City (TW)

(72) Inventors: Yao-Sheng Chou, Taipei City (TW); Hsiao-Yi Lin, Taipei City (TW); Yen-Han Chou, Taoyuan City (TW)

(73) Assignee: Decentralized Biotechnology Intelligence Co., Ltd., Taipei City (TW)

( * ) Notice: Subject to any disclaimer, the term of this patent is extended or adjusted under 35 U.S.C. 154(b) by 542 days.

(21) Appl. No.: 17/966,832

(22) Filed: Oct. 15, 2022

(65) Prior Publication Data

US 2023/0218261 A1     Jul. 13, 2023

(30) Foreign Application Priority Data

Jan. 7, 2022    (TW) .................................. 111100799

(51) Int. Cl.
*A61B 7/04*        (2006.01)
*A61B 7/00*        (2006.01)
*G10K 11/178*        (2006.01)

(52) U.S. Cl.
CPC .......... *A61B 7/04* (2013.01); *G10K 11/17853* (2018.01)

(58) Field of Classification Search
CPC ... G10L 21/0208; G10L 21/0264; A61B 7/04; A61B 7/00
See application file for complete search history.

(56) References Cited

U.S. PATENT DOCUMENTS

| | | | | |
|---|---|---|---|---|
| 5,952,618 | A | * | 9/1999 | Deslauriers ............ A61B 7/026 |
| | | | | 181/131 |
| 2006/0198533 | A1 | * | 9/2006 | Wang ..................... A61B 7/003 |
| | | | | 381/94.1 |
| 2008/0013747 | A1 | * | 1/2008 | Tran ........................ A61B 7/04 |
| | | | | 381/67 |
| 2019/0133548 | A1 | * | 5/2019 | Cai ........................ A61B 5/318 |

FOREIGN PATENT DOCUMENTS

WO        WO-2020222844 A1 * 11/2020    ....... G10K 11/17821

* cited by examiner

*Primary Examiner* — Brian T Gedeon
(74) *Attorney, Agent, or Firm* — WPAT, P.C.; Anthony King

(57)        ABSTRACT

The present invention discloses a smart noise reduction device including a control device; an audio waveform pattern recognizer coupled to the control device for identifying an audio mixed signal including a regularity signal and a non-regularity signal; an audio waveform pattern database coupled to the control device, including at least one audio type, each having a plurality of preset second regularity signals; and an audio filter coupled to the control device to obtain the regularity signal.

12 Claims, 4 Drawing Sheets

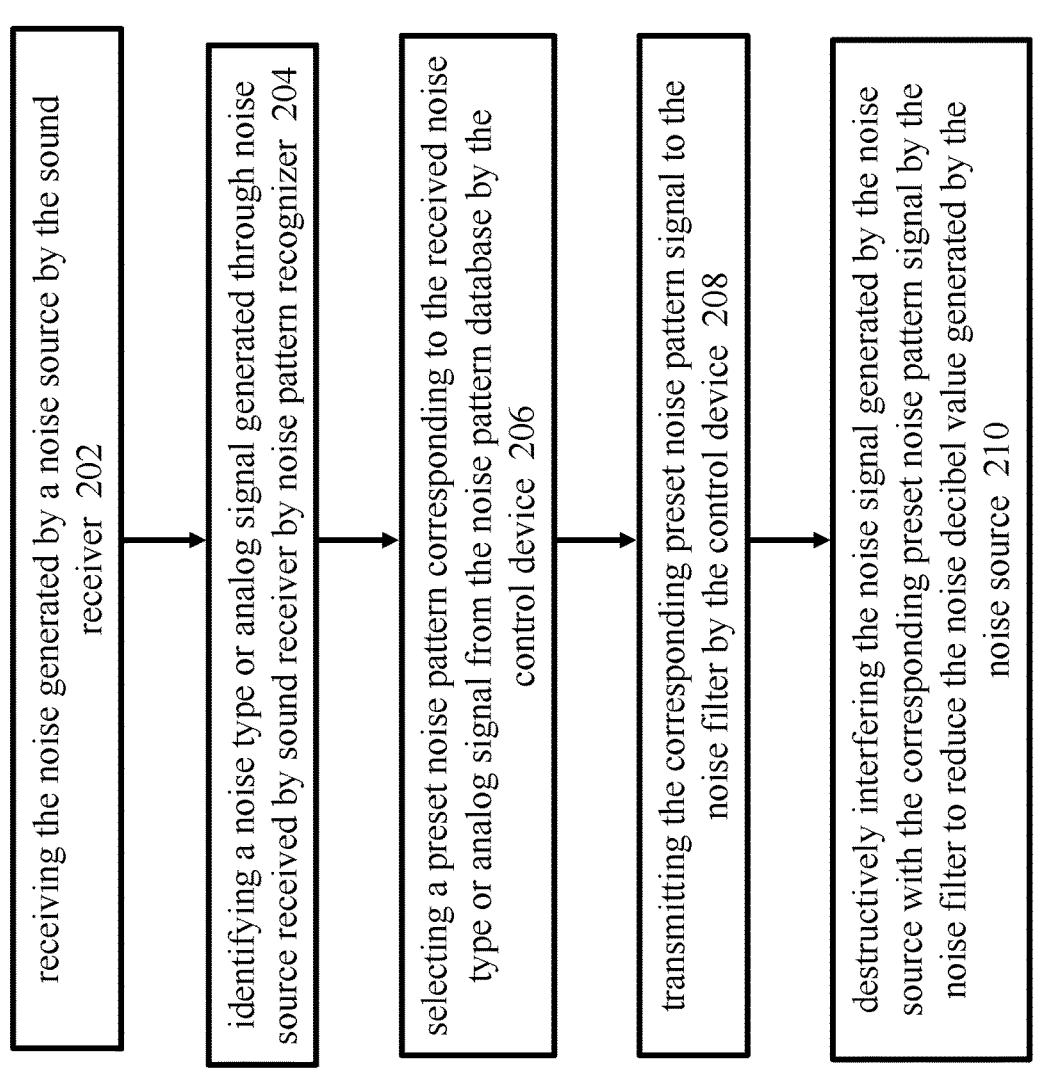

receiving the noise generated by a noise source by the sound receiver  202 identifying a noise type or analog signal generated through noise source received by sound receiver by noise pattern recognizer  204 selecting a preset noise pattern corresponding to the received noise type or analog signal from the noise pattern database by the control device  206 transmitting the corresponding preset noise pattern signal to the noise filter by the control device  208 destructively interfering the noise signal generated by the noise source with the corresponding preset noise pattern signal by the noise filter to reduce the noise decibel value generated by the noise source  210

Fig. 2

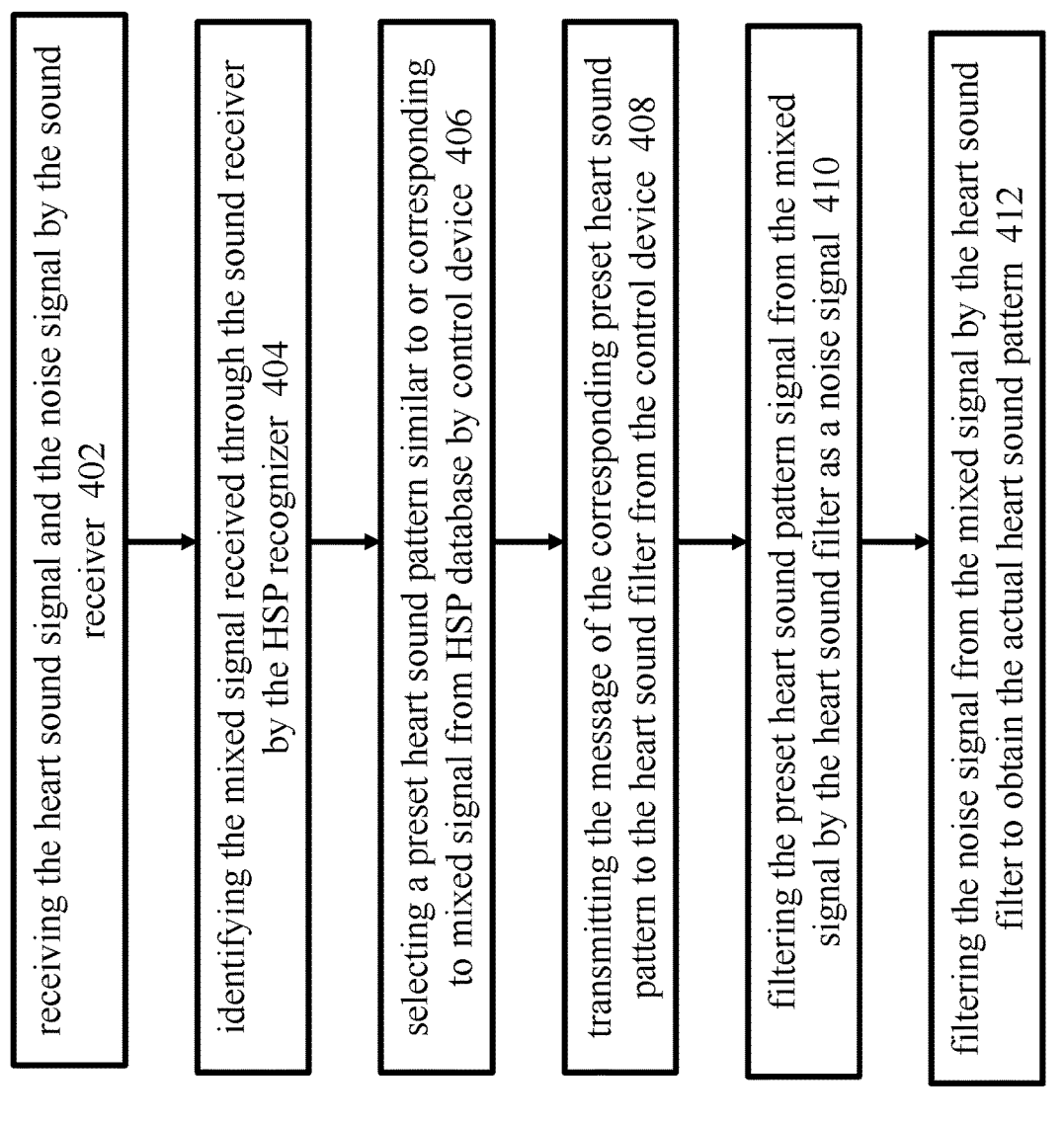

receiving the heart sound signal and the noise signal by the sound receiver  402 identifying the mixed signal received through the sound receiver by the HSP recognizer  404 selecting a preset heart sound pattern similar to or corresponding to mixed signal from HSP database by control device  406 transmitting the message of the corresponding preset heart sound pattern to the heart sound filter from the control device  408 filtering the preset heart sound pattern signal from the mixed signal by the heart sound filter as a noise signal  410 filtering the noise signal from the mixed signal by the heart sound filter to obtain the actual heart sound pattern  412

Fig. 4

SMART NOISE REDUCTION DEVICE AND THE METHOD THEREOF

CROSS-REFERENCE STATEMENT

The present application is based on, and claims priority from, Taiwan Patent Application Serial Number 111100799, filed Jan. 7, 2022, the disclosure of which is hereby incorporated by reference herein in its entirety.

BACKGROUND

1. Technical Field

The present invention relates to a noise reduction, more specifically, a method of noise reduction for an intelligent network communication.

2. Related Art

Conventional technologies of background noise cancellation are mostly used in telephone communication or headphones. The main purpose of these technologies is to prevent the impact of background noise or ambient noise on communication quality or sound quality of headphone. At present, most of the common technologies of background noise cancellation used by intelligent devices based on voice interaction are derived from the existing technologies of traditional telephone communication. These technologies include spectral subtraction, Wiener filtering and adaptive noise cancellation.

The method of spectral subtraction is to use the mean value of amplitude of speech segmentation to subtract the amplitude of non-speech segmentation to obtain the mean value of noise, and then eliminate the noise. This method has a poor effect for unsteady noise, which is easy to cause speech distortion by noise elimination, and resulting in the decline of speech recognition rate.

The method of Wiener filtering uses the transfer function of Wiener filter to convolute the mean value of noise amplitude with the amplitude of speech segmentation to obtain the amplitude information of signal by noise elimination. It does not cause serious speech distortion in Wiener filtering method, and can effectively suppress the noise with small change range or stable in the environment. However, this method estimates the mean value of noise by calculating the statistical average of the power spectrum of noise during the silent period. This estimation is based on the premise that the power spectrum of noise does not change much before and after the sound producing. Therefore, in the case of unsteady noise with large changes, this method cannot achieve higher noise reduction performance.

Another cancellation method of ambient noise commonly used in smart devices is adaptive noise cancellation method by a directional microphone. This method uses an omnidirectional microphone to collect ambient noise, a directional microphone to collect user voice, and then adaptive noise cancellation is performed for the two signals to obtain pure voice signals.

In addition, most machines or electronic equipment often produce noise during operation. For example, with the rapid development of air conditioning technology, it has been widely used in various industrial technologies and fields. The well-known air conditioning system has a compressor as the operation core, and the most important work in the system is the transfer of heat. When the compressor operates by the rotating shaft and the refrigerant is discharged, it is easy to produce vibration and noise. Although there are some means for reducing the noise, it is still unable to eliminate the noise. In order to achieve a good suppression of the noise generated during the operation of the machine or electronic equipment, the present invention has been disclosed.

SUMMARY

Based on the above-mentioned, the method of noise reduction for intelligent network communication has become an important work in many fields. For example, a database of noise reduction parameters or noise reduction levels of various noise sources are established to facilitate flexible adjustment of noise reduction levels, improve the performance of noise reduction to achieve the purpose of the present invention.

The purpose of the present invention is to provide a noise reduction device and method for improving the performance of noise reduction, especially a device for detecting heart sound. If the device is close to the body near the heart, the sound receiving device may receive the noise generated by the friction sound of clothes, which may affect the correct interpretation of signal or data.

According to one aspect of the present invention, the mixed audio signal includes an inverse noise of ambient noise. When the input noise pattern/waveform signal (inverse noise) and the noise source enter the ear canal of human together, the inverted noise and the noise source will produce destructive interference because of mutual cancellation of the waveform, so as to achieve the performance of reducing the noise decibel. By using the recursive method to limit the frequency step by step, the noise generated by the noise source can be effectively suppressed to improve the performance of noise reduction. It should be understood that the inverse noise can completely offset the noise of the noise source, and can also partially offset the noise of the noise source.

According to another aspect of the present invention, a smart noise reduction device is provided, which comprises a control device. A noise pattern recognizer is coupled to the control device, identifying a noise signal generated through a noise source received by a sound receiver. A noise pattern database is coupled to the control device, wherein the noise pattern database includes at least one audio type, each audio type having a plurality of preset noise pattern signals. A noise filter is coupled to the control device, destructively interfering the noise signal with a selected one of the plurality of preset noise pattern signals to reduce a noise decibel value generated by the noise source.

According to one aspect of the present invention, a speaker is coupled the control device to output the noise signal. An application (APP) is coupled to the control device, wherein the index of target noise reduction level is set in the application (APP).

According to another aspect of the present invention, the plurality of preset noise patterns generate a noise reduction parameter library and the noise reduction parameter library includes a plurality of indexes of noise reduction level and noise reduction parameters.

According to yet another aspect of the present invention, a smart noise reduction device is provided, which comprises a control device. An audio pattern recognizer is coupled to the control device, identifying an audio mixed signal received by a sound receiver, wherein the audio mixed signals include a first regularity pattern signal and a non-regularity pattern signal. An audio pattern database is coupled to the control device, wherein the audio pattern database includes at least one audio type, each audio type having a plurality of preset second regularity pattern signals. A noise filter is coupled to the control device, destructively interfering the audio mixed signal with a selected one of the plurality of preset second regularity pattern signals to produce an approximate noise, and destructively interfering the approximate noise with the audio mixed signals to produce the first regularity pattern signal.

According to an aspect of the present invention, a heart sound sensing device is provided, which comprises a control device. A heart sound pattern recognizer is coupled to the control device, identifying a heart sound mixed signal received by a sound receiver, wherein the heart sound mixed signals include a first regularity pattern signal and a non-regularity pattern signal. A heart sound pattern database is coupled to the control device, wherein the heart sound pattern database includes a plurality of preset second regularity heart sound pattern signals. A heart sound filter is coupled to the control device, destructively interfering the heart sound mixed signal with a selected one of the plurality of preset second regularity heart sound pattern signals to produce an approximate noise, and destructively interfering the approximate noise with the heart sound mixed signals to produce the first regularity heart sound pattern signal.

According to another aspect of the present invention, a wireless transmission device is coupled to the control device such that data of the heart sound patterns database can be received from a remote server or a remote device through the wireless transmission device. An analog-to-digital converter is coupled to the control device such that the heart sound pattern can be converted into a digital heart sound signal.

According to another aspect of the present invention, a warning device is coupled to the control device which can prompt the user's heartbeat status and heartbeat frequency data.

According to another aspect of the present invention, a computer program/algorithm is used to select the preset second regularity heart sound pattern signal corresponding to the first regularity pattern signal.

BRIEF DESCRIPTION OF THE DRAWINGS

FIG. 2 shows a flow diagram of a method of intelligent noise reduction according to an embodiment of the present invention;

FIG. 4 illustrates a flow diagram of a method of intelligent noise reduction according to another embodiment of the present invention.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

Figure 1:
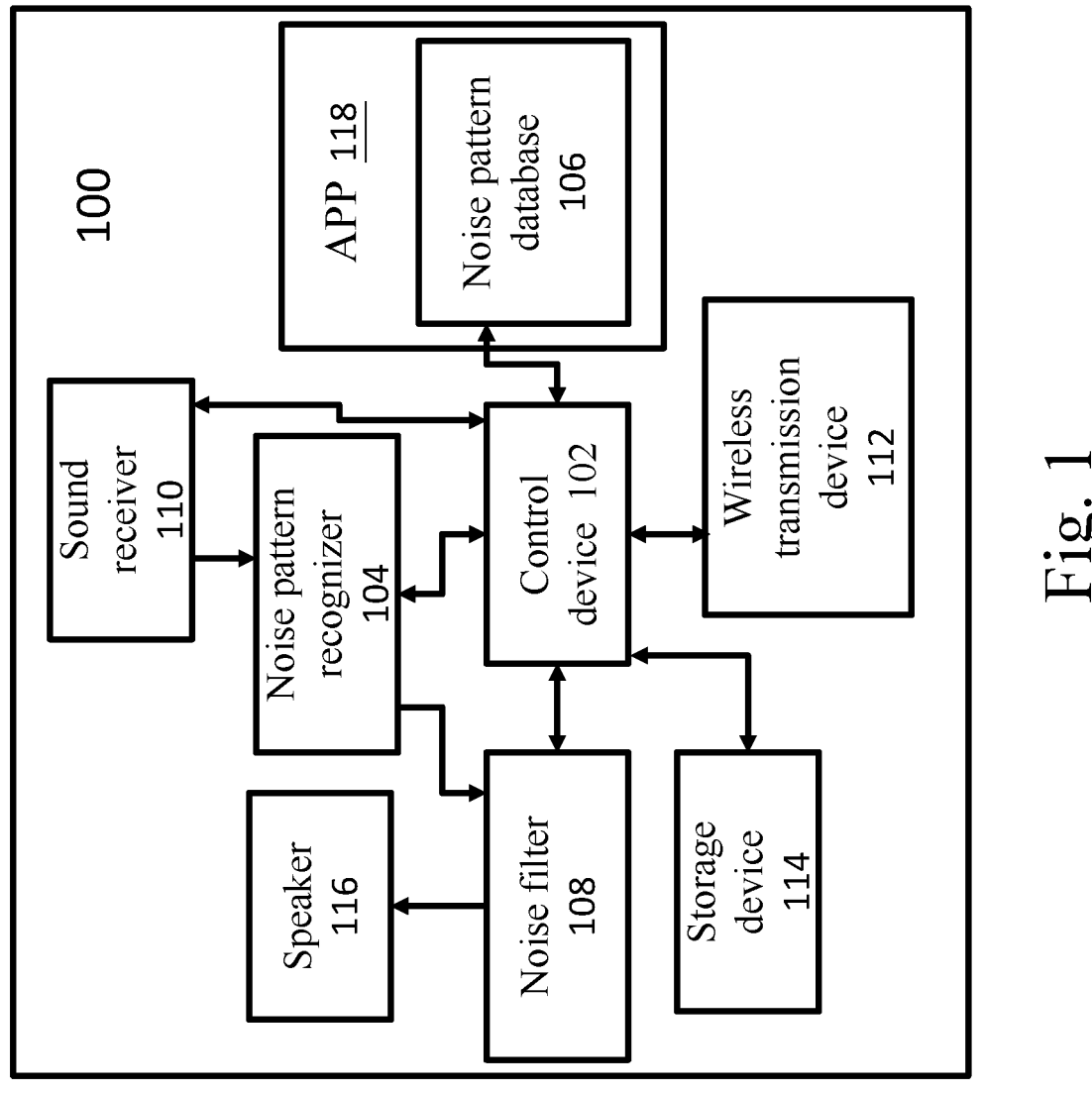
FIG. 1 shows a functional block diagram of a smart noise reduction device according to one embodiment of the present invention.

As shown in FIG. 1, it is a functional block diagram of a smart noise reduction device according to one embodiment of the present invention. In the present embodiment, the smart noise reduction device 100 is capable of eliminating noise generated from various machines, apparatus and/or equipment. For example, this noise source refers to the noise generated by the machine, apparatus or equipment, such as range hood, grounding machine, air conditioner, washing machine, etc. The smart noise reduction device 100 may be built-in or externally configured on the above machine, apparatus, or equipment. The smart noise reduction device 100 includes a control device 102, a noise pattern recognizer (audio pattern recognizer) 104, a noise pattern database (audio pattern database) 106, a noise filter 108, a sound receiver 110, a wireless transmission device 112, a storage device 114, a speaker 116. The control device 102 is coupled with the noise pattern recognizer 104, the noise pattern database 106, the noise filter 108, the sound receiver 110, the wireless transmission device 112, the storage device 114 and the speaker 116 to process or control the operations of these elements. In one embodiment, the control device 102 is a processor. The sound receiver 110 is, for example, a microphone. The noise pattern recognizer 104 is coupled to the noise filter 108 and the sound receiver 110. The noise filter 108 is coupled to the speaker 116. The function of the noise filter 108 is employed to offset the noise signal generated by the noise source against the corresponding noise pattern (waveform pattern) signal to reduce the noise decibel value (dB value) generated by the noise source.

Referring to FIG. 1, the sound receiver 110 is used to receive the noise generated by external noise sources and output an analog signal of the noise. The sound receiver is, for example, a microphone. Among them, noise patterns of various noise sources are stored in the noise pattern database 106, and a parameter library for various noise reduction is generated based on the noise patterns. The parameter library of noise reduction includes the corresponding relationship between the indexes of noise reduction level and the parameters of noise reduction. For example, an index of noise reduction level corresponds to a parameter of noise reduction. In one embodiment, the parameter library of noise reduction includes 32 indexes of noise reduction level, which corresponds to 32 groups of noise reduction parameter, in which the index 1 of noise reduction level corresponds to the noise reduction parameter 1, the index 2 of noise reduction level corresponds to the noise reduction parameter 2, . . . , the index 32 of noise reduction level corresponds to the noise reduction parameter 32, and so on. Generally speaking, the noise reduction parameter can be a set of parameters, including multiple filter coefficients. The noise pattern recognizer 104 identifies the noise analog signal generated by the noise source received through the sound receiver 110. In another example, if the noise pattern database 106 does not have a preset noise model (pattern), the new noise model (pattern) is automatically stored for subsequent noise reduction. For example, an ambient noise is detected before playing music by an audio device in outdoor, in which noise is reduced during playing and the noise model is refreshed in the playing interval of the music. In addition, it is also applicable to play the on-ship audio device. Although this will not completely reduce noise, it will effectively improve the signal-to-noise ratio. In other words, the above-mentioned is applicable to the application of noise reduction in open space. Then, the received noise signal (X) is identified by the noise pattern recognizer 104, and the preset noise pattern (AL) corresponding to the received noise signal (X) is selected from the noise pattern database 106 by the control device 102. The message of the corresponding noise pattern (AL) is transmitted to the noise filter 108 by the control device 102. In order to reduce the noise generated by the noise source, after selecting the corresponding noise pattern (AL) signal through the control device 102, the noise signal (X) is offset against the corresponding noise pattern (AL) signal by the noise filter 108 and then outputs through the speaker 116. In one embodiment, data of the noise pattern database 106 may be received from a remote server or a remote device through the wireless transmission device 112. In one embodiment, the noise pattern database 106 may also be stored in the storage device 114.

The index of target noise reduction level may be received through the wireless transmission device 112. In one embodiment, the index of target noise reduction level is set in the application (APP) 118 of the noise reduction device 100 which is transmitted to the wireless transmission device 112 through the wireless network. The noise pattern database 106 is integrated into the APP 118. For example, the wireless networks include various wireless specifications, such as Bluetooth, WLAN, WiFi, etc. The index of target noise reduction level is used to determine the target noise reduction level and the target noise reduction parameter corresponding to the target noise reduction level. The target noise reduction parameters are that match the noise level generated by the noise source. In other words, the inverse noise obtained after processing based on the target noise reduction parameters can offset the noise generated by the noise source to the greatest extent.

In one embodiment, the opening or closing the function of noise reduction is controlled by the noise reduction APP 118 of the smart noise reduction device 100, and the target noise reduction level is set by the APP 118, which is suitable for different noise levels generated by various noise sources. For example, the user can select an appropriate noise reduction level for the noise source by adjusting a noise reduction level adjuster of the APP 118 to achieve the best performance of noise reduction. In other words, the best performance of noise reduction can be achieved by adjusting the noise reduction level to correct the noise difference. The index value of noise reduction level is related to the noise level.

As shown in FIG. 2, it shows a flow diagram of a method of intelligent noise reduction according to an embodiment of the present invention. In this embodiment, the method of intelligent noise reduction includes the following steps. First, in the step 202, the sound receiver 110 receives the noise generated by a noise source. Various machines, devices and/or equipment are the source of the noise, for example, including range hood, grounding machine, air conditioners, washing machines, etc. The continuous noise is generated by these machines, devices or equipment during operation. The sound receiver 110 receives the noise generated by the noise source. Then, in the step 204, a noise type or analog signal generated through the noise source received by the sound receiver 110 is identified by the noise pattern recognizer 104. Next, in the step 206, a preset noise pattern corresponding to the received noise type or analog signal is selected from the noise pattern database 106 by the control device 102. Subsequently, in the step 208, the corresponding preset noise pattern signal is transmitted to the noise filter 108 by the control device 102. Finally, in the step 210, the noise signal generated by the noise source is destructively interferes with the corresponding preset noise pattern signal by the noise filter 108 to reduce the noise decibel value (dB value) generated by the noise source.

Figure 3:
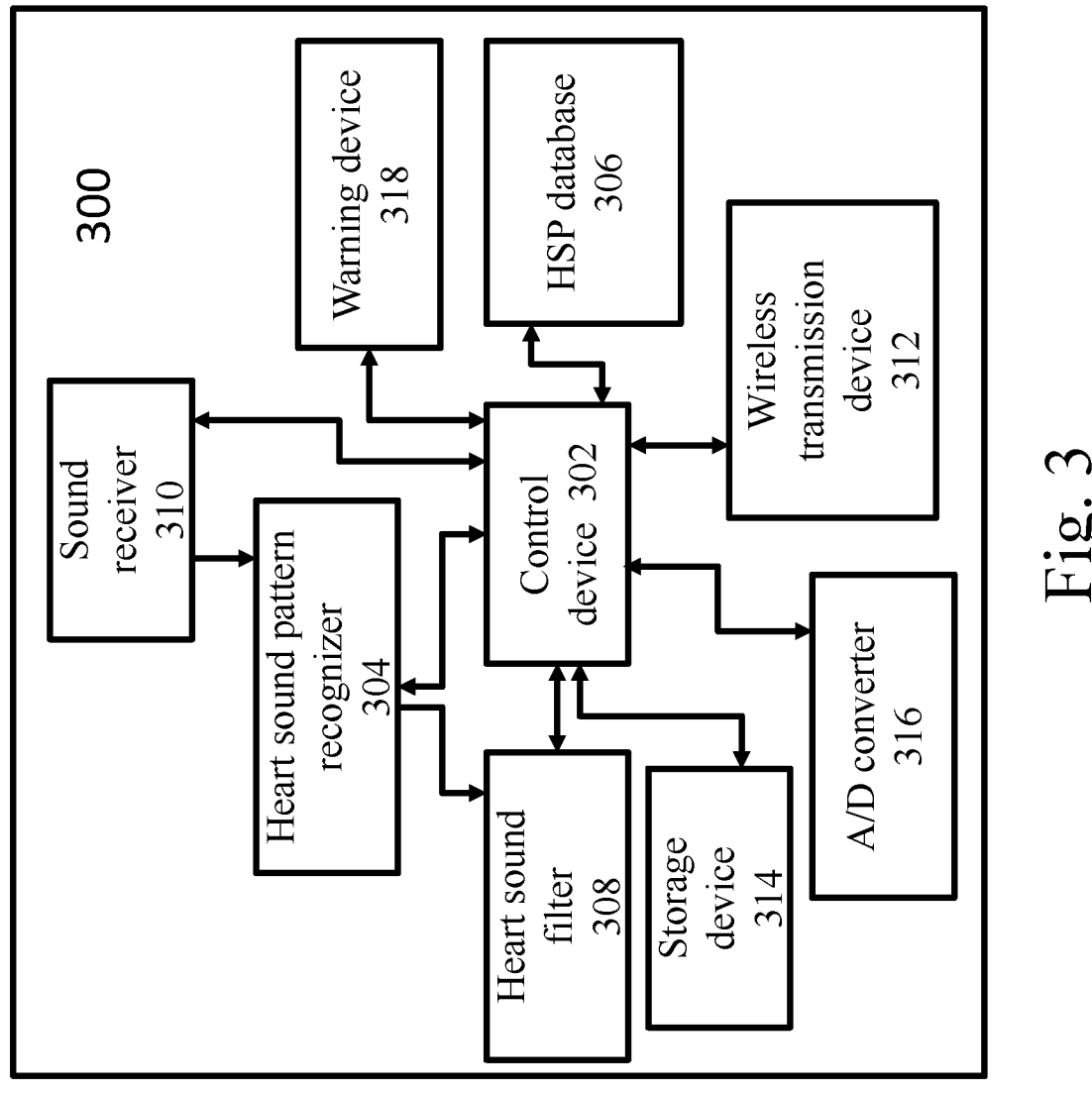
FIG. 3 shows a functional block diagram of a smart noise reduction device according to another embodiment of the present invention.

As shown in FIG. 3, it is a functional block diagram of a smart noise reduction device according to another embodiment of the present invention. According to the above principles and designs for various functions, it can be applied to a sensing device for heart sound, which is beneficial to the application of medical devices. In this embodiment, the smart noise reduction device 300 is built into a heart sound sensing device to detect the heart sound. When the smart noise reduction device 300 is close to the body near the heart, the sound receiver may receive irregular clothing friction sound during actual detection, which may affect the correct interpretation of signal. Therefore, the smart noise reduction device 300 of the invention is used to filter out the noise such as the friction sound of clothes by the heart sound filter, which can make the device stick near the heart, reduce or eliminate the noise generated by clothes, and achieve the effect of correctly reading the heartbeat sound wave. The smart noise reduction device 300 includes a control device 302, a heart sound pattern recognizer 304, a heart sound pattern (HSP) database 306, a heart sound filter 308, a sound receiver 310, a wireless transmission device 312, a storage device 314, an A/D converter 316 and a warning device 318. The control device 302 is coupled with the HSP recognizer 304, the HSP database 306, the heart sound filter 308, the sound receiver 310, the wireless transmission device 312, the storage device 314, the A/D converter 316 and the warning device 318 to process or control the operations of these elements. In one embodiment, the control device 302 is a processor. The heart sound filter 308 is coupled to the HSP recognizer 304 and the A/D converter 316. The HSP recognizer 304 is coupled to the sound receiver 310.

Referring to FIG. 3, the sound receiver 310 is used to attach the body or clothes near the user's heart, detect the heartbeat sound in the heart, and output an analog signal. The sound receiver 310 is coupled to the control device 302, and it can be a microphone. In actual operation, the analog signals received by the sound receiver 310 include heart sound signals in the heart and noise signals. The analog signal received by the sound receiver 310 is identified by the HSP recognizer 304, which is a mixed signal (X) containing the actual heart sound signal (AA) and the noise signal (N). The mixed signal (X) includes a regular signal (repeated or regular heart sound signal AA) and an irregular waveform pattern or irregular signal (noise signal N). Generally speaking, the actual heart sound (cardiogram) signal (AA) is a regular and waveform signal, and the mixed signal (X) contains regular heart sound signal (AA). Therefore, there may be similar regular waveform signal or irregular state, depending on the noise type. Therefore, the mixed signal (X) is identified by the HSP recognizer 304, a preset heart sound pattern (AL) similar to or corresponding to the mixed signal (X) is selected from the HSP database 306 by the control device 302 as the simulated corresponding heart sound pattern, which is one of many phonocardiograms or signals pre-stored in the HSP database 306.

The message of the preset heart sound pattern (AL) is transmitted to the heart sound filter 308 by the control device 302. In order to obtain the actual heart sound signal, after selecting the preset heart sound pattern/waveform (AL) through the control device 302, the heart sound filter 308 filters the preset heart sound pattern (AL) signal from the mixed signal (X) as a noise signal (N). Then, the heart sound filter 308 filters out the noise signal (N) from the mixed signal (X) as the actual heart sound pattern (AA). That is, the actual phonocardiogram (AA) is equal to (mixed signal X) subtracting (mixed signal X subtracting preset heart sound pattern signal AL). In another embodiment, the actually received heart sound pattern/waveform (AR) is equal to (mixed signal X plus target heart sound pattern signal AL) subtracting (mixed signal X). The above operations are processed by using the principle of destructive interference of sound waves.

In one embodiment, data of the HSP database 306 may be received from a remote server or a remote device through the wireless transmission device 312. In another embodiment, the HSP database 306 may also be stored in the storage device 314.

The above-mentioned processes include identifying the mixed signal (X) by the HSP recognizer 304, selecting the target heart sound pattern (AL) corresponding to the mixed signal (X) by the control device 302, and subtracting the noise signal (N) from the mixed signal (X) by the heart sound filter 308. The actual heart sound pattern/waveform (AA) can be obtained by the above three steps, and the heart sound filter 308 outputs the actual heart sound pattern/waveform (AA) to the analog-to-digital converter 316. After conversion by the analog-to-digital converter 316, the actual heart sound pattern (AA) can be converted into a digital heart sound signal that conforms to a predetermined frequency range. That is, an analog heart sound signal conforming to a predetermined frequency range is output after the heart sound filter 308 filters out the noise signal not within a predetermined frequency range. In one embodiment, the working frequency range of the heart sound is 20 Hz to 1000 Hz, and the sound signal is output by an analog signal. The analog-to-digital converter 316 receives a filter signal of the heart sound filter 308 to obtain an analog heart sound signal with a predetermined frequency range, converts it into a digital heart sound signal conforming to the predetermined frequency range, and outputs it to the control device 302. In one embodiment, the analog-to-digital converter 316 may be built-in or external to the control device 302.

In the method of heart sound sensing, first, the heart sound sensing device 300 is placed close to the user's heart to capture an analog heart sound signal. Generally speaking, the signal waveform detection is to analyze whether the waveform of the user's cardiac signals includes a first heart sound (cardiac) signal S1 and a second heart sound (cardiac) signal S2 with a signal strength less than that of the first heart sound (cardiac) signal S1. However, if the second heart sound signal S2 is not detected, the test results of this method will not be affected, so the second heart sound signal S2 is not a necessary test condition. A dynamic detection threshold is added to analyze the first heart sound signal S 1. This dynamic detection threshold will automatically adjust the detection threshold based on the intensity change of the background noise and the previous peak intensity value of the first heart sound signal, so as to accurately determine the peak intensity of the first heart sound signal. In this embodiment, the envelope waveform is obtained by capturing the envelope of the signal, and it is compared whether the envelope waveforms of the first heart signal S1 and the second heart signal S2 in the section are continuous and the same. Then, the signal pulse detection is to analyze whether the heartbeat frequency of the heart sound signals is between 40 and 300 times per minute, analyze the peak time difference of two adjacent first heart sound signals, calculate the heartbeat frequency per minute based on the peak time difference, and distinguish the first heart sound, find the peak intensity and occurrence time of the first heart sound by using the dynamic threshold method, and thereby calculating the heartbeat frequency per minute.

The control device 302 operates and processes the digital heart sound signal conforming to the predetermined frequency range output by the HSP recognizer 304 to obtain the peak intensity and time value of the first heart sound, records the signal-to-noise ratio value at each measurement location, compares the signal-to-noise ratio value and outputs an optimal measurement location, calculates the user's heartbeat frequency per minute, and outputs the heartbeat frequency value per minute. The control device 302 may have a built-in or external memory device. The recording device receives the digital heart sound signal conforming to the operating frequency and records it in the storage device 314. The warning device 318 receives the value of the digital heart sound signal output by the control device 302 to prompt the user's heartbeat status and heartbeat frequency data. For example, if the heartbeat frequency data is abnormal received by the warning device 318, the abnormal heartbeat frequency data may be transmitted to an external device through the wireless transmission unit 312. In another embodiment, the warning device 318 may be a light emitting diode (LED) or a buzzer to indicate an abnormal heartbeat condition.

As shown in FIG. 4, it illustrates a flow diagram of a method of smart noise reduction according to another embodiment of the present invention. In this embodiment, the method of smart noise reduction comprises the following steps. First, in the step 402, the heart sound signal and the noise signal are received by the sound receiver 310. This heart sound signal is the beating signal continuously generated by the user's heart. Then, in the step 404, the analog signal received through the sound receiver 310 is identified by the HSP recognizer 304, wherein the analog signal is the mixed signal (X) including the actual heart sound signal (AA) and the noise signal (N). Next, in the step 406, a preset heart sound pattern similar to or corresponding to the mixed signal is selected from the heart sound pattern (HSP) database 306 by the control device 302. In the following step 408, the message of the corresponding preset heart sound pattern is transmitted to the heart sound filter 308 from the control device 302. Subsequently, in the step 410, the heart sound filter 308 filters out the preset heart sound pattern (AL) signal from the mixed signal (X) as a noise signal. That is, the heart sound mixed signal (X) is destructively interfered with one of a plurality of preset regular heart sound pattern signals to generate an approximate noise. Finally, in the step 412, the noise signal (N) is filtered from the mixed signal (X) by the heart sound filter 308 to obtain the actual heart sound pattern. That is, the approximate noise is destructively interfered with the heart sound mixed signal (X) to produce a regular heart sound pattern signal.

The smart noise reduction devices 100, 300 are configured to communicate with external devices, which may be external computing devices, computing systems, mobile devices (smart phones, tablets, smart watches), or other types of electronic devices.

External devices include computing core, user interface, Internet interface, wireless communication transceiver and storage device. The user interface includes one or more input devices (e.g., keyboard, touch screen, voice input device), one or more audio output devices (e.g., speaker) and/or one or more visual output devices (e.g., video graphics display, touch screen). The Internet interface includes one or more networking devices (e.g., wireless local area network (WLAN) devices, wired LAN devices, wireless wide area network (WWAN) devices). The storage device includes a flash memory device, one or more hard disk drives, one or more solid-state storage devices and/or cloud storage devices.

The computing core includes processors and other computing core components. Other computing core components include video graphics processors, memory controllers, main memory (e.g., RAM), one or more input/output (I/O) device interface modules, input/output (I/O) interfaces, input/output (I/O) controllers, peripheral device interfaces, one or more USB interface modules, one or more network interface modules, one or more memory interface modules, and/or one or more peripheral device interface modules.

The external device processes the data transmitted by the wireless transmission device 112, 312 to produce various results.

As will be understood by persons skilled in the art, the foregoing preferred embodiment of the present invention illustrates the present invention rather than limiting the present invention. Having described the invention in connection with a preferred embodiment, modifications will be suggested to those skilled in the art. Thus, the invention is not to be limited to this embodiment, but rather the invention is intended to cover various modifications and similar arrangements included within the spirit and scope of the appended claims, the scope of which should be accorded the broadest interpretation, thereby encompassing all such modifications and similar structures. While the preferred embodiment of the invention has been illustrated and described, it will be appreciated that various changes can be made without departing from the spirit and scope of the invention.

What is claimed is:

1. A smart noise reduction device, comprising:
a control device;
a microphone coupled to said control device to receive a noise;
an audio pattern database coupled to said control device, wherein said audio pattern database includes noise patterns of various noise sources, wherein a new noise pattern received by said microphone is automatically stored in said audio pattern database by said control device;

wherein a preset pattern corresponding to said noise is selected from said audio pattern database by said control device to offset said received signal to reduce a noise decibel value (dB value) generated by a noise source; and
a speaker being responsive to said processor to outputs said offset signal.

2. The device of claim 1, further comprising a wireless transmission device coupled to said control device.

3. The device of claim 1, further comprising an application (APP) coupled to said control device.

4. The device of claim 1, further comprising a storage device coupled to said control device.

5. The device of claim 1, further comprising an analog-to-digital converter coupled to said control device.

6. The device of claim 1, wherein said control device is a processor.

7. A heart sound sensing device, comprising:
a control device;
a microphone coupled to said control device to receive a signal;
a heart sound pattern (HSP) database coupled to said control device, wherein said heart sound pattern database includes heart sound patterns;
wherein a preset heart sound pattern similar to or corresponding to said received signal is selected from said HSP database by said control device, wherein an identified noise is identified by offsetting said received signal with said preset heart sound pattern by said control device, followed by filtering out said identified noise by a filter, thereby outputting filtered signal to an outputting device.

8. The device of claim 7, further comprising a wireless transmission device coupled to said control device.

9. The device of claim 7, further comprising a warning device coupled to said control device.

10. The device of claim 7, further comprising a storage device coupled to said control device.

11. The device of claim 7, further comprising an analog-to-digital converter coupled to said control device.

12. The device of claim 7, wherein said control device is a processor.

* * * * *